US012579643B2

(12) United States Patent
Astuto Arouche Nunes et al.

(10) Patent No.: US 12,579,643 B2
(45) Date of Patent: Mar. 17, 2026

(54) SYSTEM AND METHOD FOR ANATOMICAL FEATURES TRANSPLANTATION FOR DATA VARIETY AUGMENTATION ON MEDICAL IMAGES

(71) Applicant: GE Precision Healthcare LLC, Waukesha, WI (US)

(72) Inventors: Bruno Astuto Arouche Nunes, San Mateo, CA (US); Ravi Soni, Livermore, CA (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 302 days.

(21) Appl. No.: 18/433,689

(22) Filed: Feb. 6, 2024

(65) Prior Publication Data

US 2025/0252559 A1     Aug. 7, 2025

(51) Int. Cl.
*G06T 7/00* (2017.01)
*G06T 7/11* (2017.01)
*G16H 30/20* (2018.01)
*G16H 30/40* (2018.01)

(52) U.S. Cl.
CPC .............. *G06T 7/0012* (2013.01); *G06T 7/11* (2017.01); *G16H 30/20* (2018.01); *G16H 30/40* (2018.01); *G06T 2207/10088* (2013.01); *G06T 2207/20081* (2013.01); *G06T 2207/30096* (2013.01)

(58) Field of Classification Search
None
See application file for complete search history.

(56) References Cited

U.S. PATENT DOCUMENTS

2017/0200067 A1* 7/2017 Zhou .................... G06V 30/194
2022/0046166 A1* 2/2022 Holmstrom .......... A61B 18/148
(Continued)

FOREIGN PATENT DOCUMENTS

KR      20230125509 A  *  3/2023  ............. A61B 5/055

OTHER PUBLICATIONS

"Less is More: Unsupervised Mask-guided Annotated CT Image Synthesis with Minimum Manual Segmentations"; Xing et al, IEEE Transactions on Medical Imaging; 2017. (Year: 2017).*
(Continued)

*Primary Examiner* — David Ometz
(74) *Attorney, Agent, or Firm* — Fletcher Yoder, P.C.

(57)          ABSTRACT

A method includes segmenting a region of interest in an anatomical region in both a source imaging data and a destination imaging data, wherein different regions of the region of interest are labeled with different segmentation masks. The method includes selecting a region from the different regions from the source imaging data and spatially matching the region to a corresponding region in the destination imaging data. The method includes determining a spatial intersection between the region and the corresponding region. The method includes utilizing an intersection mask to crop a first portion of the region from the source imaging data and utilizing the intersection mask to remove a second portion of the destination imaging data in the corresponding region. The method includes adding the first portion of the region from the source imaging data into the destination imaging data where the second portion was removed.

20 Claims, 15 Drawing Sheets

(56) References Cited

U.S. PATENT DOCUMENTS

| 2024/0127429 A1* | 4/2024 | Lee | ........................ | G06T 7/0012 |
| 2024/0203567 A1* | 6/2024 | Ruiz | ..................... | G06T 7/0012 |

OTHER PUBLICATIONS

"Unsupervised Medical Image Segmentation with Adversarial Networks: From Edge Diagrams to Segmentation Maps"; Sivanesan et al; Nov. 14, 2019 (Year: 2019).*
"TricycleGAN: Unsupervised Image Synthesis and Segmentation Based on Shape Priors"; Sivanesan et al; Feb. 5, 2021. (Year : 2021).*
Austo, PhD et al., "Automatic Deep Learning-assisted Detection and Grading of Abnormalities in Knee MRI Studies," Radiology: Artificial Intelligence, 2021, 12 pgs.
Schütte et al., "Overcoming barriers to data sharing with medical image generation: a comprehensive evaluation," NPJ | Digital Medicine, 2021, 14 pgs.

* cited by examiner

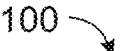
100
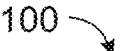
FIG. 1

Segmentation Labels: ○ Meniscus Label  ● Femoral Cartilage Label  ⬤ Tibial Cartilage Label From One Class to 4 Classes 244    246    248

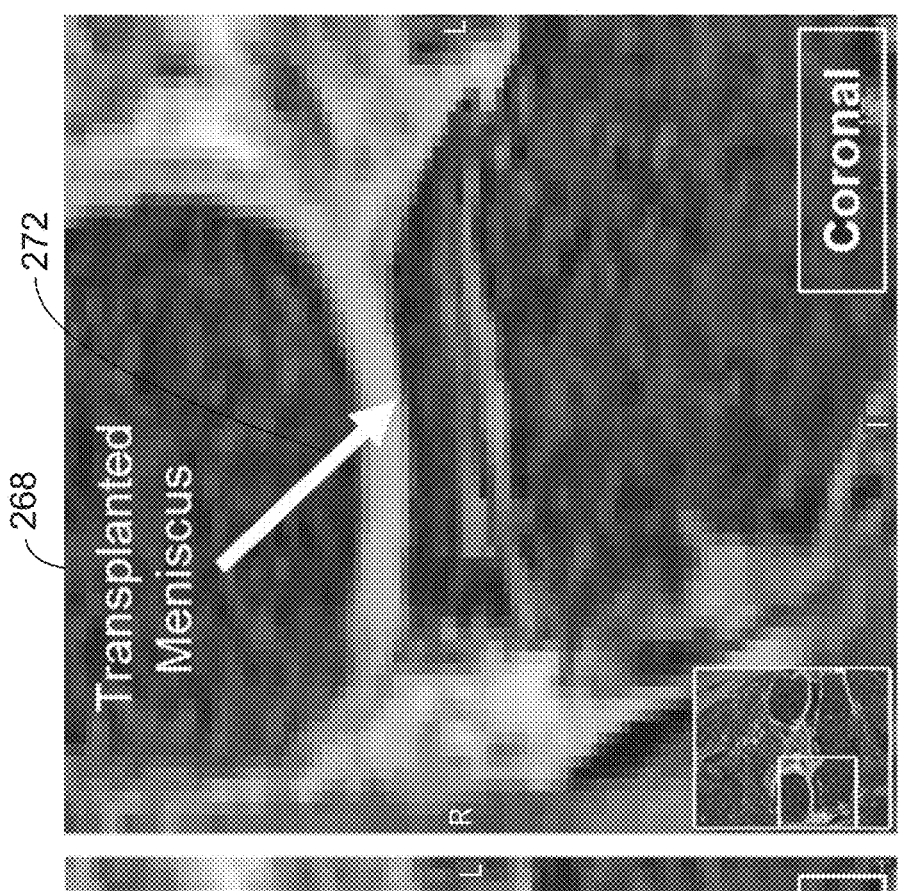
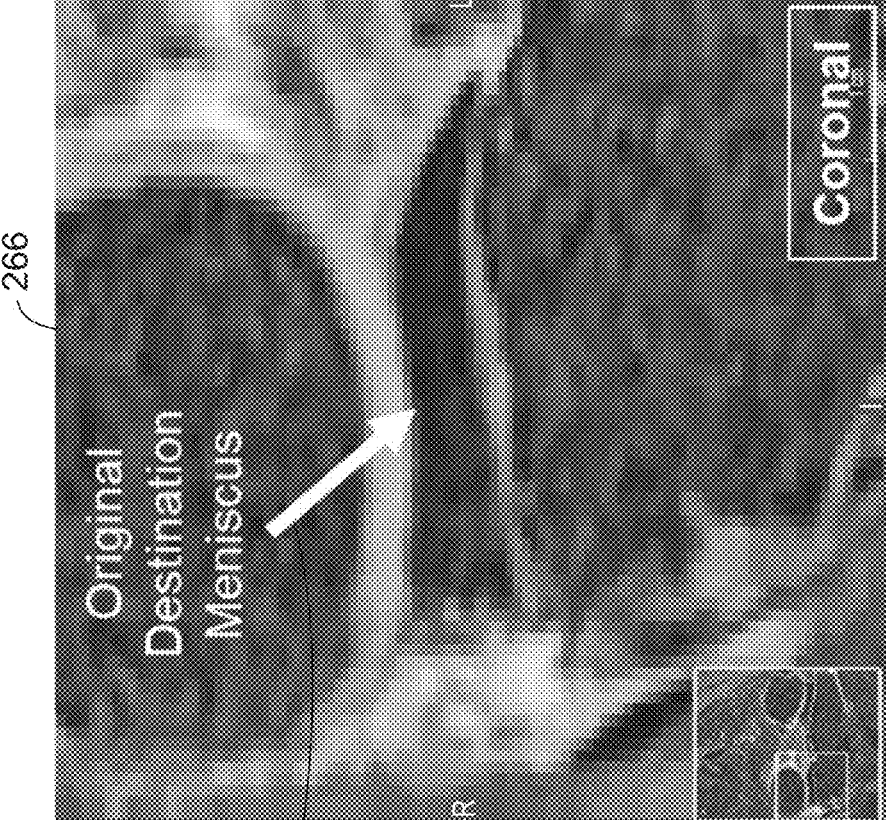
FIG. 9

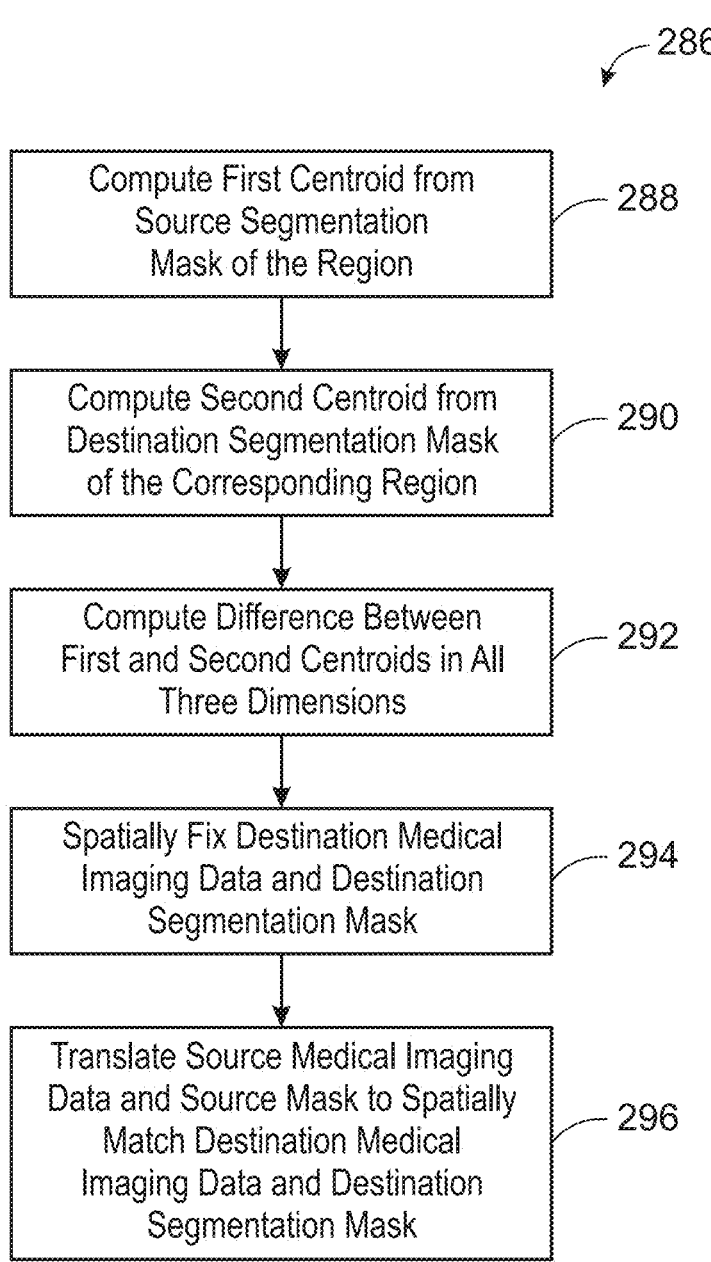

286

Compute First Centroid from
Source Segmentation
Mask of the Region — 288

Compute Second Centroid from
Destination Segmentation Mask
of the Corresponding Region — 290

Compute Difference Between
First and Second Centroids in All
Three Dimensions — 292

Spatially Fix Destination Medical
Imaging Data and Destination
Segmentation Mask — 294

Translate Source Medical Imaging
Data and Source Mask to Spatially
Match Destination Medical
Imaging Data and Destination
Segmentation Mask — 296

FIG. 11

Segmentation Labels: ○ Meniscus Label ● Femoral Cartilage Label ● Tibial Cartilage Label

SYSTEM AND METHOD FOR ANATOMICAL FEATURES TRANSPLANTATION FOR DATA VARIETY AUGMENTATION ON MEDICAL IMAGES

BACKGROUND

The subject matter disclosed herein relates to medical imaging and, more particularly, to a system and a method for anatomical features transplantation for data variety augmentation on medical images.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During magnetic resonance imaging (MRI), when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

Accurate segmentation of tissue (e.g., cartilage and meniscus) in the knee joint is of clinical interest for morphometric assessment of cartilage structure and to assess cartilage thickness as longitudinal changes in cartilage thickness have been associated with osteoarthritis incidence. Accurate whole knee joint tissue segmentation from three-dimensional (3D) MRI is challenging. Recently, deep learning-based algorithms have been utilized for whole knee joint tissue segmentation. However, the accuracy of the deep learning-based models is impacted greatly by variations in the data used to train such models. In particular, deep learning-based segmentation models can fail occasionally, for example, when some image features were not seen by the model during training and could not be generalized from the set of cases it has seen during training. For example, in some cases, the presence of meniscus lesions causes the model to make incorrect decisions such as not segmenting the meniscus tissue or segmenting around the lesion. In theory, the greater and more diverse the training set is, the more robust and generalizable the model is and the higher is its performance.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for generating a variety of data for training a deep learning-based segmentation model is provided. The computer-implemented method includes obtaining, at a processor, both a source medical imaging volume and a destination medical imaging volume having an anatomical region. The computer-implemented method also includes segmenting, via the processor, a region of interest in the anatomical region in both the source medical imaging volume and the destination medical imaging volume, wherein the region of interest is labeled with a single segmentation mask. The computer-implemented method further includes determining, via the processor, a laterality of the anatomical region in both the source medical imaging volume and the destination medical imaging volume. The computer-implemented method even further includes converting, via the processor, the single segmentation mask to a multi-class segmentation mask based on the laterality so that different regions of the region of interest are labeled with different segmentation masks for both the source medical imaging volume and the destination medical imaging volume. The computer-implemented method still further includes selecting, via the processor, a region from the different regions from the source medical imaging volume for transplantation. The computer-implemented method yet further includes spatially matching, via the processor, the region in the source medical imaging volume to a corresponding region in the destination medical imaging volume. The computer-implemented method further includes determining, via the processor, a spatial intersection between the region in the source medical imaging volume and the corresponding region in the destination medical imaging volume utilizing respective segmentation masks for the region and the corresponding region. The computer-implemented method even further includes utilizing, via the processor, an intersection mask of the spatial intersection to crop a first portion of the region overlapping with the intersection mask from the source medical imaging volume for transplantation in the destination medical imaging volume. The computer-implemented method yet further includes utilizing, via the processor, the intersection mask of the spatial intersection to remove a second portion of the destination medical imaging volume in the corresponding region that overlaps with the intersection mask. The computer-implemented method further includes adding, via the processor, the first portion of the region from the source medical imaging volume into the destination medical imaging volume where the second portion was removed to generate an augmented version of the destination medical imaging volume.

In another embodiment, a system for generating a variety of data for training a deep learning-based segmentation model is provided. The system includes a memory encoding processor-executable routines. The system also includes a processor configured to access the memory and to execute the processor-executable routines, wherein the routines, when executed by the processor, cause the processor to perform actions. The actions include obtaining both a source medical imaging data and a destination medical imaging data having an anatomical region. The actions also include segmenting a region of interest in the anatomical region in both the source medical imaging data and the destination medical imaging data, wherein the region of interest is labeled with a single segmentation mask. The actions further include determining a laterality of the anatomical region in both the source medical imaging data and the destination medical imaging data. The actions even further include converting the single segmentation mask to a multi-class segmentation mask based on the laterality so that different regions of the region of interest are labeled with different segmentation masks for both the source medical imaging data and the destination medical imaging data. The actions still further include selecting a region from the different regions from the source medical imaging data for transplantation. The actions yet further include spatially matching the region in the source medical imaging data to a corresponding region in the destination medical imaging data. The actions further include determining a spatial intersection between the region in the source medical imaging data and the corresponding region in the destination medical imaging data utilizing respective segmentation masks for the region and the corresponding region. The actions even further include utilizing an intersection mask of the spatial intersection to crop a first portion of the region overlapping with the spatial intersection mask from the source medical imaging data for transplantation in the destination medical imaging data. The actions yet further include utilizing the intersection mask of the spatial intersection to remove a second portion of the destination medical imaging data in the corresponding region that overlaps with the spatial intersection mask. The actions further include adding the first portion of the region from the source medical imaging data into the destination medical imaging data where the second portion was removed to generate an augmented version of the destination medical imaging data.

In a further embodiment, a non-transitory computer-readable medium, the computer-readable medium including processor-executable code that when executed by a processor, causes the processor to perform actions. The actions include obtaining both a source medical imaging data and a destination medical imaging data having an anatomical region. The actions also include segmenting a region of interest in the anatomical region in both the source medical imaging data and the destination medical imaging data, wherein the region of interest is labeled with a single segmentation mask. The actions further include determining a laterality of the anatomical region in both the source medical imaging data and the destination medical imaging data. The actions even further include converting the single segmentation mask to a multi-class segmentation mask based on the laterality so that different regions of the region of interest are labeled with different segmentation masks for both the source medical imaging data and the destination medical imaging data. The actions still further include selecting a region from the different regions from the source medical imaging data for transplantation. The actions yet further include spatially matching the region in the source medical imaging data to a corresponding region in the destination medical imaging data. The actions further include determining a spatial intersection between the region in the source medical imaging data and the corresponding region in the destination medical imaging data utilizing respective segmentation masks for the region and the corresponding region. The actions even further include utilizing an intersection mask of the spatial intersection to crop a first portion of the region overlapping with the intersection mask from the source medical imaging data for transplantation in the destination medical imaging data. The actions yet further include utilizing the intersection mask of the spatial intersection to remove a second portion of the destination medical imaging data in the corresponding region that overlaps with the intersection mask. The actions further include adding the first portion of the region from the source medical imaging data into the destination medical imaging data where the second portion was removed to generate an augmented version of the destination medical imaging data.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 1 illustrates a schematic diagram of a magnetic resonance imaging (MRI) system suitable for use with the disclosed techniques;

FIG. 9 depicts coronal views of a destination MR image of a knee and an augmented version of the destination MR image, in accordance with aspects of the present disclosure;

FIG. 11 illustrates a flow diagram of a method for spatially matching a region in a source medical imaging volume to a corresponding region in a destination medical imaging volume, in accordance with aspects of the present disclosure;

DETAILED DESCRIPTION

Figure 2:
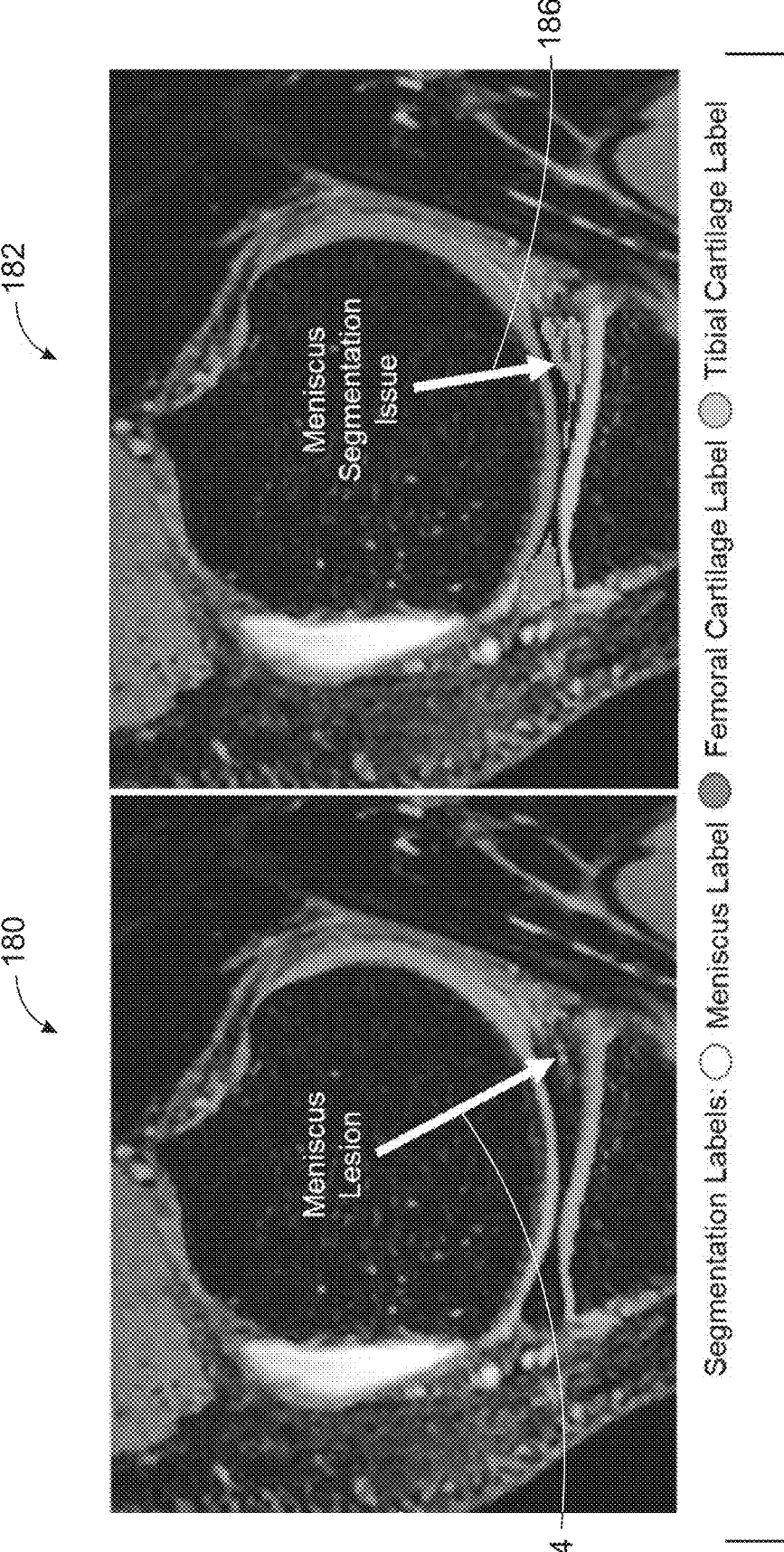
FIG. 2 depicts examples of MR images without segmentation masks and with segmentation masks.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

Deep learning (DL) approaches discussed herein may be based on artificial neural networks, and may therefore encompass one or more of deep neural networks, fully connected networks, convolutional neural networks (CNNs), transformer-based networks, unrolled neural networks, perceptrons, encoders-decoders, recurrent networks, wavelet filter banks, u-nets, general adversarial networks (GANs), dense neural networks, or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for anatomical features (e.g., meniscus features) transplantation for data variety augmentation on medical images (e.g., 3D knee MR imaging volumes or two-dimensional (2D) knee MR images). In particular, the present disclosure provides systems and methods for generating a variety of data for training a deep learning-based segmentation model. For example, the systems and methods include obtaining both a source medical imaging data (e.g., image or imaging volume) and a destination medical imaging data (e.g., image or imaging volume) having an anatomical region. The systems and methods also include segmenting a region of interest in the anatomical region in both the source medical imaging data and the destination medical imaging data (e.g., utilizing a trained deep learning-based segmentation model or non-deep learning-based segmentation technique or model), wherein the region of interest is labeled with a single segmentation mask. The systems and methods further include determining a laterality of the anatomical region in both the source medical imaging data and the destination medical imaging data. The systems and methods even further include converting the single segmentation mask to a multi-class segmentation mask so that different regions of the region of interest are labeled with different segmentation masks for both the source medical imaging data and the destination medical imaging data. The systems and methods still further include selecting a region from the different regions from the source medical imaging data for transplantation. The systems and methods yet further include spatially matching the region in the source medical imaging data to a corresponding region in the destination medical imaging data. The systems and methods further include determining a spatial intersection between the region in the source medical imaging data and the corresponding region in the destination medical imaging data utilizing respective segmentation masks for the region and the corresponding region. The systems and methods even further include utilizing an intersection mask of the spatial intersection to crop a first portion of the region overlapping with the intersection mask from the source medical imaging data for transplantation in the destination medical imaging data. The systems and methods yet further include utilizing the intersection mask of the spatial intersection to remove a second portion of the destination medical imaging data in the corresponding region that overlaps with the intersection mask. The systems and methods further include adding the first portion of the region from the source medical imaging data into the destination medical imaging data where the second portion was removed to generate an augmented version of the destination medical imaging data.

In certain embodiments, the source medical imaging data (e.g., source medical imaging volume) and the destination medical imaging volume (e.g., source medical imaging data) are magnetic resonance imaging volumes (e.g., acquired with a MR scanner utilizing a 3D fast spin echo sequence such as CUBE from General Electric Healthcare). In certain embodiments, the medical imaging data for the knee may be acquired with a different MRI sequence. In certain embodiments, the imaging data may be two-dimensional (2D) imaging data. In certain embodiments, the region of interest includes a meniscus, the anatomical region includes a knee, and the different regions include different meniscus horns (e.g., lateral anterior horn, lateral posterior horn, medial anterior horn, and medial posterior horn). In certain embodiments, the different regions may include portions of the meniscus body. In certain embodiments, the region selected from the different regions includes a meniscus horn having a lesion and the corresponding region includes a corresponding meniscus horn to the meniscus horn having the lesion, and the corresponding meniscus horn lacks a lesion.

In certain embodiments, the systems and methods include utilizing the augmented version of the destination medical imaging data to update training of the trained deep learning-based segmentation model to be configured to segment meniscus horns having lesions. In certain embodiments, spatially matching the region in the source medical imaging data to the corresponding region in the destination medical imaging data includes computing a first centroid from a source segmentation mask of the region; computing a second centroid from a destination segmentation mask of the corresponding region; computing a Cartesian difference between the first centroid and the second centroid in all three dimensions; spatially fixing the destination medical imaging data and the destination segmentation mask; and translating the source medical imaging data and the source segmentation mask to spatially match with the destination medical imaging data and the destination segmentation mask utilizing the Cartesian difference between the first centroid and the second centroid in all three dimensions.

In certain embodiments, utilizing the intersection mask of the spatial intersection to crop the first portion of the region overlapping with the intersection mask from the source medical imaging data includes multiplying the source medical imaging data by an intersecting data corresponding to the intersection mask to generate a first imaging data where only pixel intensities of pixels (e.g., 2D pixel or 3D pixel (i.e., a voxel)) of the source medical imaging data within the intersection mask are kept. In certain embodiments, utilizing the intersection mask of the spatial intersection to remove a second portion of the destination medical imaging data in the corresponding region that overlaps with the intersection mask includes multiplying the destination medical imaging data by an inverse of the intersecting data to generate a second imaging data where pixel intensities of pixels of the destination medical imaging data outside the intersection mask are kept and pixels within the intersection mask are zeroed out.

The disclosed embodiments provide for a topological-based methodology for augmenting (e.g., both automatically and artificially) a training set and increasing data variety (which in turn increase segmentation model accuracy). In particular, the disclosed embodiments enable augmentation of MRI 3D datasets of the knee (e.g., acquired with a 3D fast spin echo sequence) or MRI 2D datasets of the knee with many instances of different type of menisci by copying this region of interest from one case and seamlessly pasting it in another case. The disclosed embodiments enable the copying of lesions from cases where there are known menisci lesions and include lesions in other where the menisci are healthy. The disclosed embodiments provide an augmentation technique that increases data variety by increasing the representativeness of lesion patterns that are less common for anomaly detection (i.e., lesion detection). The disclosed embodiments utilize real image features from multiple sources and combine them into one modified/augmented new image, thus, avoiding the drawbacks of generative-adversarial techniques that generate artificial medical images (i.e., creating image features that are not representative real life). The disclosed embodiments reduce cost and save time by avoiding having to collect extra data or manually labeling more data, while also increasing the performance of existing deep learning-based segmentation models (via increasing the variety of data for training). The disclosed embodiments increase both quantitatively and qualitatively the accuracy of the deep learning-based segmentation compared to the original deep-learning based segmentation approaches. The disclosed embodiments provide more accurate thickness measurements and better localized anomaly detection due to more accurate segmentations, thus, benefiting the patient.

Although the techniques described below are utilized for generating a variety of data for training (or update the training of) a deep learning-based segmentation model for the segmentation of the meniscus of the knee, the techniques may be utilized for other deep-learning segmentations models trained to segment regions of interest in other types of anatomical regions. In addition, although the disclosed techniques are utilized on 3D MRI datasets, the techniques may be utilized for other types of 3D medical imaging data (e.g., 3D tomographic data). In addition, in the following, the term "source" refers to a 3D MRI data where the meniscus is going to be extracted from, while the term "destination" refers to a 3D MRI data that is going to receive the cut (extracted) meniscus from the source. Also, the techniques described below may be utilized with 2D MRI datasets.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to generate a variety of data for training a deep learning-based segmentation model as described below. In certain embodiments, the memory circuit 170 may store one or more neural networks (e.g., deep learning-based segmentation network for a knee or other anatomical region). In certain embodiments, the disclosed techniques may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

FIG. 2 is an example of an MR image 180 without segmentation masks and an MR image 182 (e.g., same image) with segmentation masks. The MR images 180, 182 are sagittal slices of a knee acquired with an MR scanner utilizing a 3D fast spin echo sequence. Menisci are soft tissue present in the knee joint that are normally characterized in MR images acquired with a fat saturated 3D fast spin echo sequence as a dark triangular shaped structure between the femur condyles and the tibia. Lesions of the meniscus are characterized by structures inside of the meniscus with a brighter signal. Arrow 184 indicates a meniscus lesion present in the MR image 180. Sometimes lesions on the meniscus can lead to errors in segmentation. For example, in the MR image 182, a trained deep learning-based segmentation model segmented around the lesion on the medial posterior meniscus horn (as indicated by arrow 186), as the meniscus is normally a dark region in the image. In particular, as shown in the MR image 182, the brighter signal of the lesion was dimmed by the trained deep learning-based segmentation model to be background and, thus, was not segmented. The error is due to certain features (e.g., meniscus lesions) being under-represented in the training datasets causing the model to not perform well. However, acquiring more data and labeling it in order to increase representativeness in the training set is expensive and impracticable. The techniques disclosed herein solve this problem by increasing the variety of data and image features that the models are exposed to during training, by intelligently and artificially introducing variety in the already available data, rather than acquiring and labeling more data.

Figure 3:
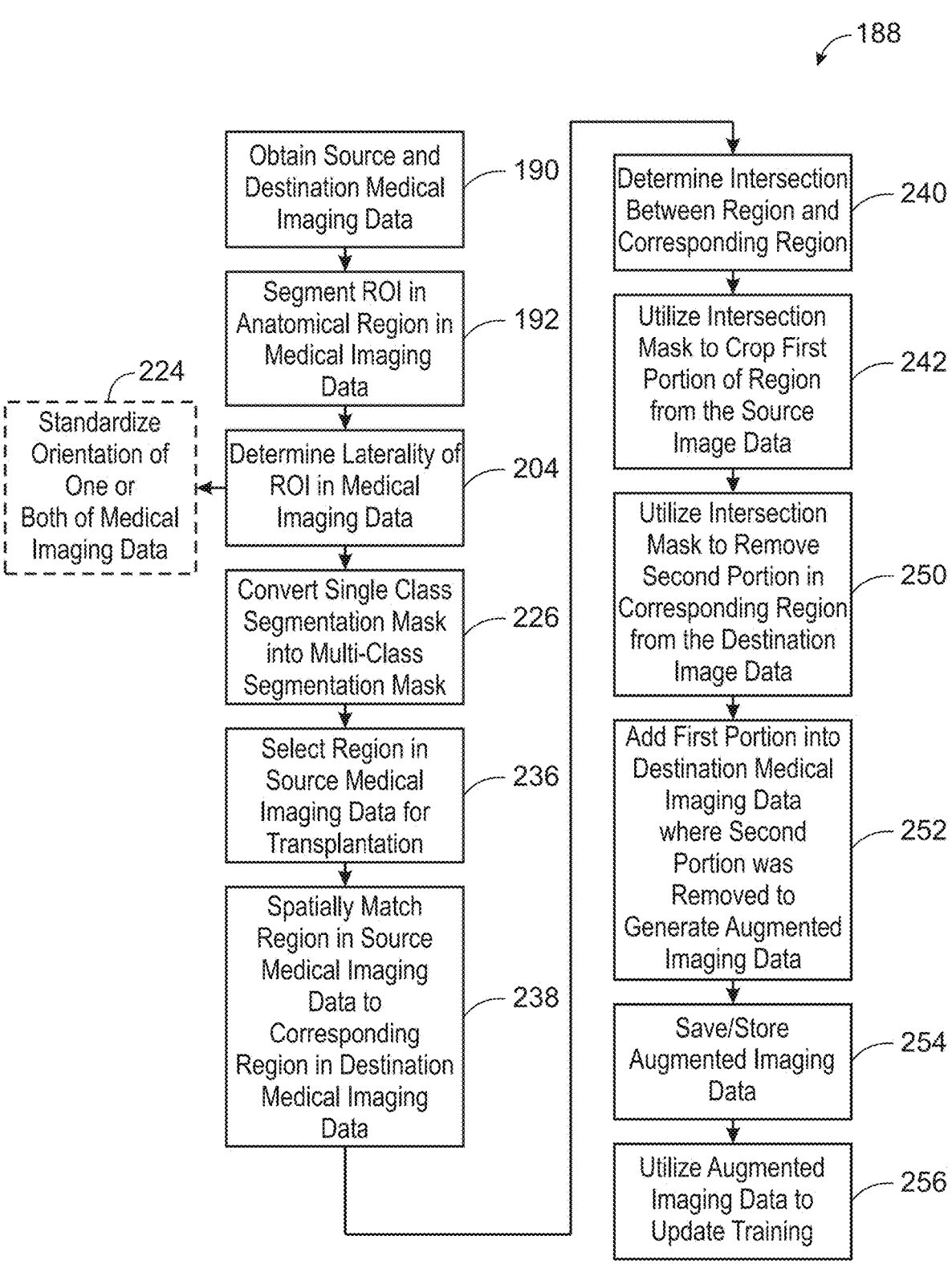
FIG. 3 illustrates a flow diagram of a method for generating a variety of data for training a deep learning-based segmentation model, in accordance with aspects of the present disclosure.

FIG. 3 illustrates a flow diagram of a method 188 for generating a variety of data for training a deep learning-based segmentation model. One or more steps of the method 188 may be performed by processing circuitry of the magnetic resonance imaging system 100 in FIG. 1 or a remote computing device. One or more of the steps of the method 188 may be performed simultaneously or in a different order from the order depicted in FIG. 3. One or more (and in some cases) all of the steps of the method 188 may be performed automatically.

Figure 4:
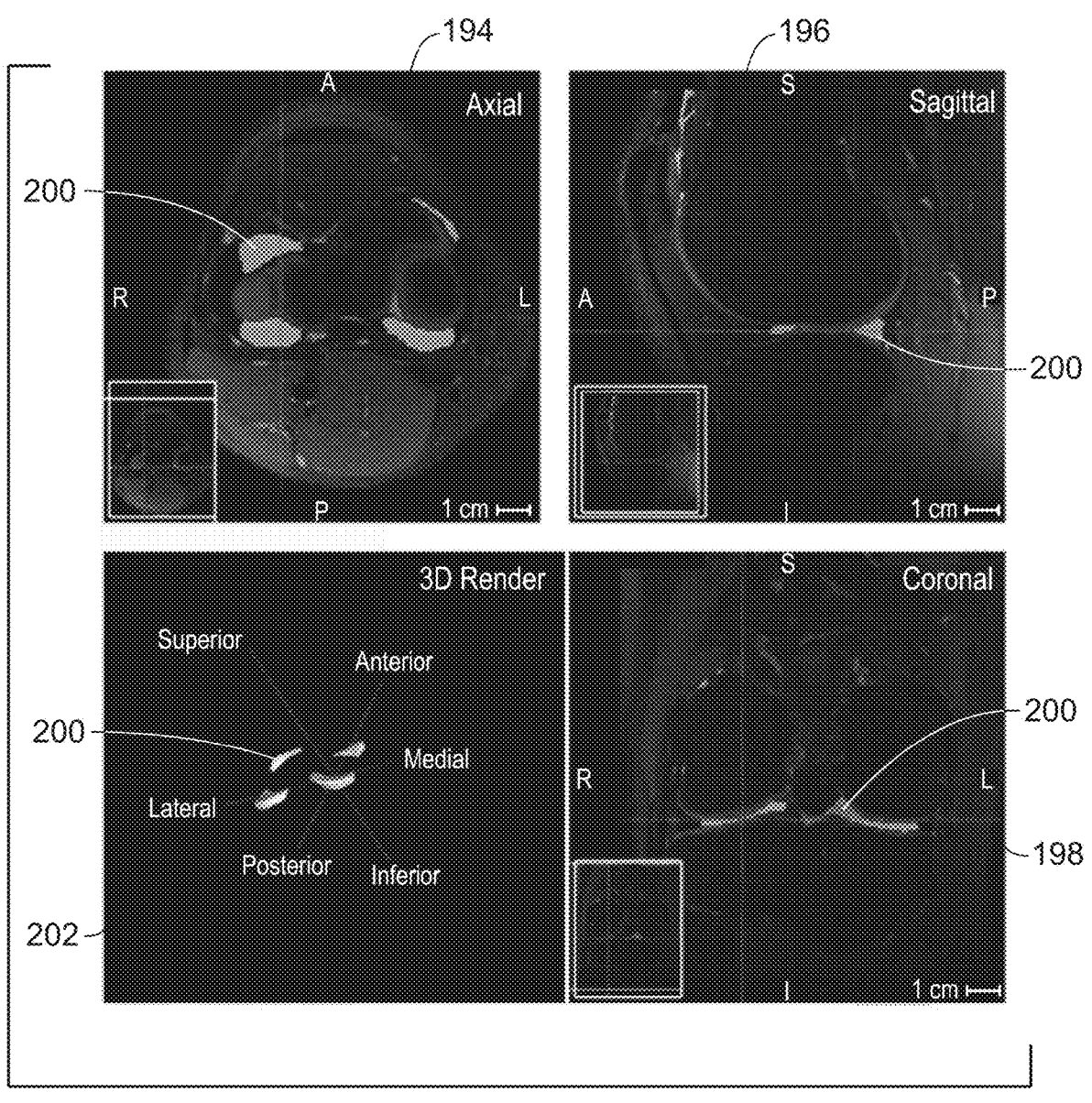
FIG. 4 depicts examples of MR images illustrating segmentation masks of the four meniscus horns of a knee in axial, sagittal and coronal views, plus the 3D rendering of such segmentation masks, in accordance with aspects of the present disclosure.

The method 188 includes obtaining both a source medical imaging data and a destination medical imaging data having an anatomical region (block 190). In certain embodiments, the source medical imaging data and the destination medical imaging data are magnetic resonance imaging data (e.g., acquired with a MR scanner utilizing a 3D fast spin echo sequence such as CUBE from General Electric Healthcare). The method 188 also includes segmenting a region of interest (ROI) in the anatomical region in both the source medical imaging data and the destination medical imaging data, wherein the region of interest is labeled with a single segmentation mask (block 192). In certain embodiments, a trained deep learning-based segmentation model (e.g., cartilage and meniscus deep-learning based segmentation model) is utilized for segmentation of the imaging data. In certain embodiments, a non-deep learning-based segmentation model or technique is utilized for segmentation of the imaging data. In certain embodiments, the region of interest includes a meniscus and the anatomical region includes a knee. FIG. 4 depicts examples of MR images 194, 196, 198 of a knee illustrating segmentation of the meniscus of a knee (e.g., segmented with a trained deep learning-based segmentation model). The MR images 194, 196, and 198 were acquired with a MR scanner utilizing a 3D fast spin echo sequence. The meniscus images 194, 196, and 198 are axial, sagittal, and coronal views, respectively, of the knee. The trained deep learning-based segmentation model is configured to infer in both a source imaging data and a destination imaging data. The trained deep learning-based segmentation model is also configured to have the meniscus segmentation masks extracted and isolated from other masks (i.e., the cartilage masks). As depicted in the MR images 194, 196, and 198, the trained deep learning-based segmentation model outputs a single segmentation mask (e.g., single class representation) for all four of the meniscus horns (i.e., as lateral anterior horn, lateral posterior horn, medial anterior horn, and medial posterior horn) as indicated by reference numeral 200. Image 202 is a 3D rendering of all four of the segmented meniscus horns alone with the single segmentation mask. In certain embodiments, the segmentation model can be trained to output 4 different classes/labels for all 4 meniscus horns. In certain embodiments, another deep learning-based model may be utilized to convert a single mask into 4 labels.

The individual meniscus horns need to be separated (i.e., distinguished) from each other. Returning to FIG. 3, the method 188 includes determining a laterality of the anatomical region in both the source medical imaging data and the destination medical imaging data (block 204). In certain embodiments, the laterality of the knee is determined (i.e., whether the knee is left (e.g., medial to lateral) or right (e.g., lateral to medial). In certain embodiments, the laterality information may be provided a priori and, thus, determined based on this information. In certain embodiments, determining laterality includes utilizing data from the Digital Imaging and Communications in Medicine (DICOM) header tags associated with the medical imaging data when laterality information is not provided a priori.

Figure 5:
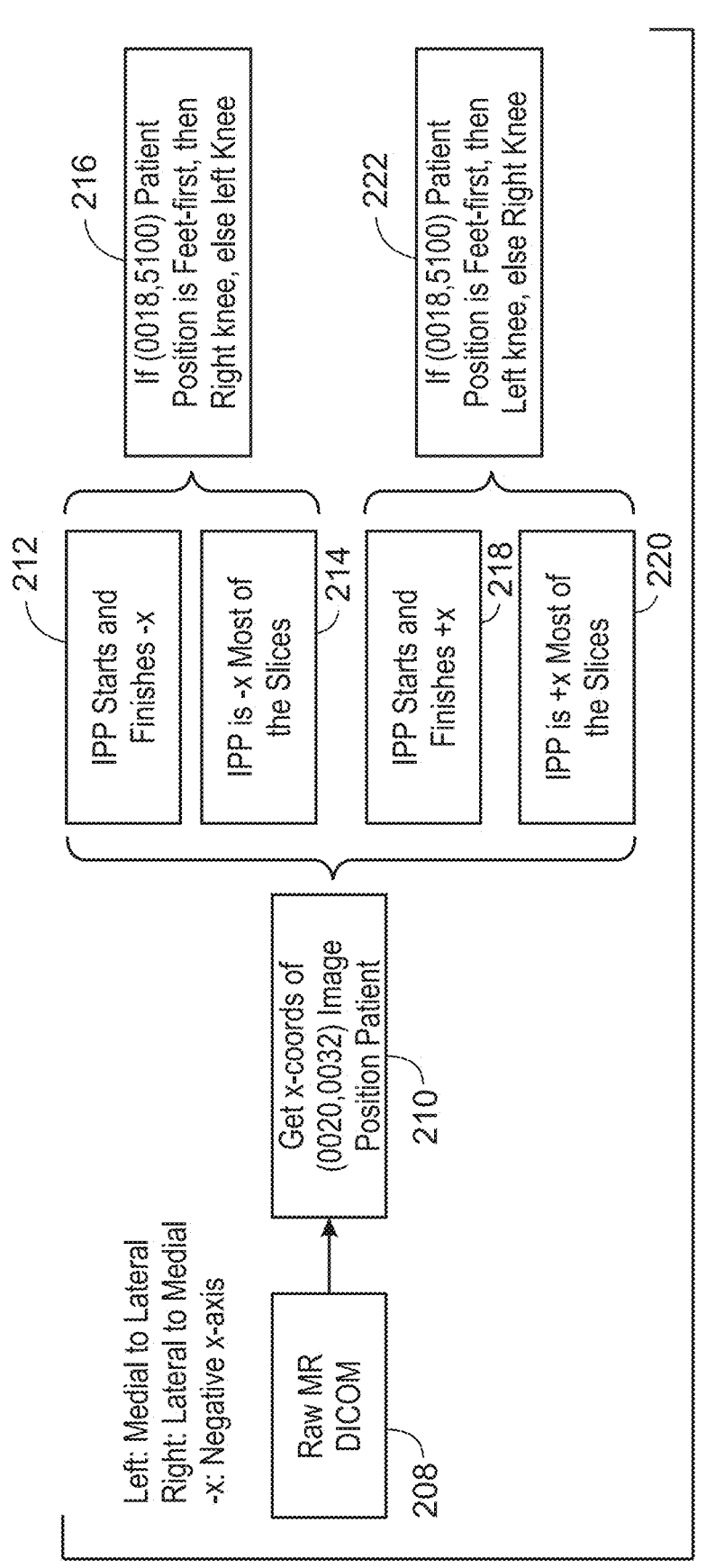
FIG. 5 is a schematic diagram illustrating the process for determining laterality, in accordance with aspects of the present disclosure.

FIG. 5 is a schematic diagram illustrating the process for determining laterality. As indicated in FIG. 5, the raw MR DICOM information is obtained as indicated by reference numeral 208. Then x-coordinates of the image patient position (IPP, which is the patient location coordinates inside the scanner) are obtained as indicated by reference numeral 210. IPP[0] (x-coordinate) increases on the direction of the left-hand side of the patient given that patient position (PP, head first or feet first) is feet first. Assuming the PP is feet first, if the IPP starts negative and finishes negative (as indicated by reference numeral 212) or if the IPP is negative for most of the slices (as indicated by reference numeral 214), then the knee is assumed right (as indicated by reference numeral 216). If the IPP starts positive and finishes positive (as indicated by reference numeral 218) or if the IPP is positive for most of the slices (as indicated by reference numeral 220), then the knee is assumed left (as indicated by reference numeral 222).

Returning to FIG. 3, in certain embodiments, when the imaging data (source imaging data and destination imaging data) is not oriented to the left, the method 188 includes standardizing the orientation of the imaging data to the left (i.e., medial to lateral) (i.e., flipping the imaging data along the z-axis) (block 224). When the imaging data is already oriented to the left, nothing is done. Both the source imaging data and destination imaging data need to be in the same orientation.

Figure 6:
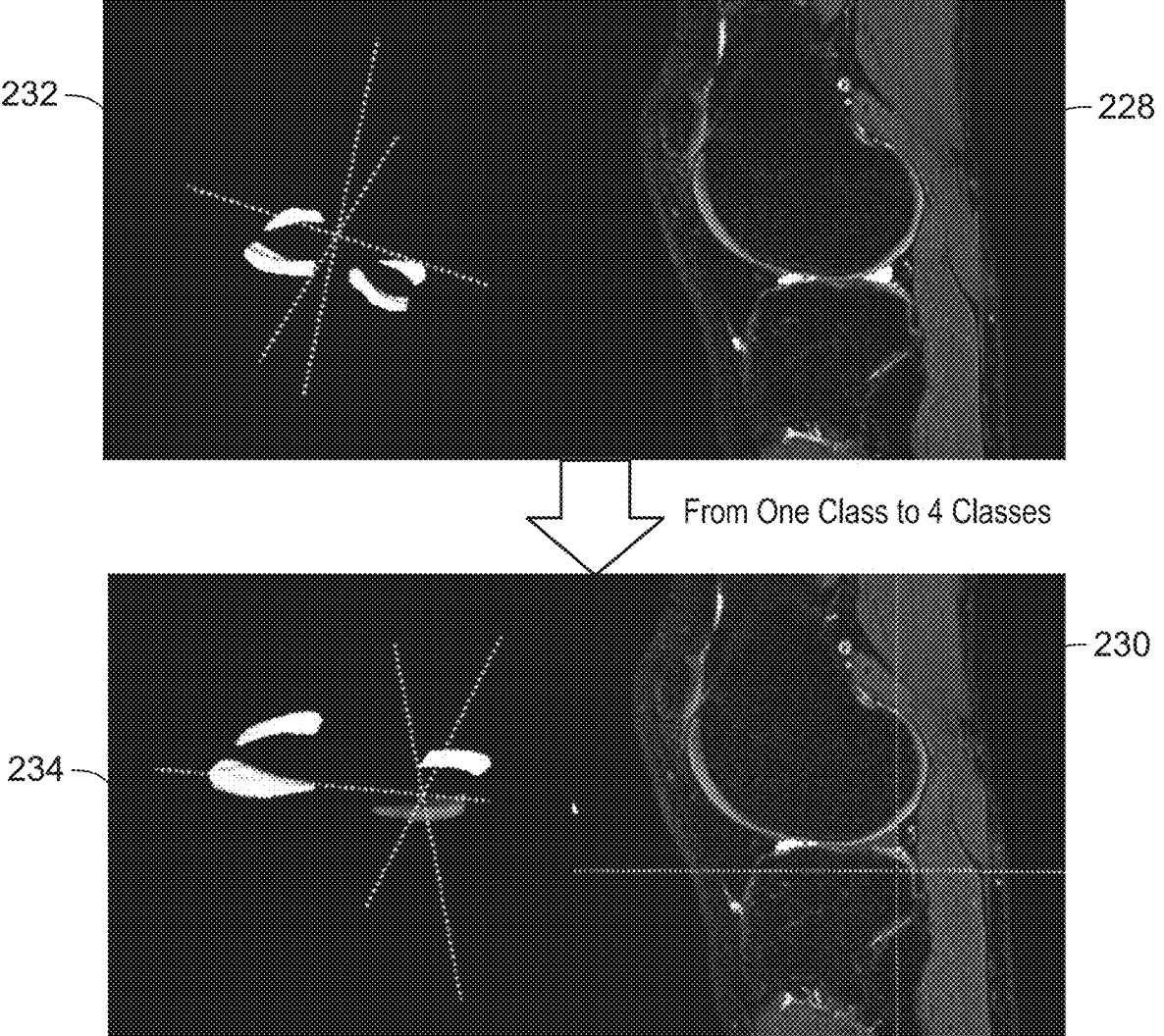
FIG. 6 depicts MR images illustrating meniscus segmentation masks converted from a single class to four classes, in accordance with aspects of the present disclosure.

With both source and destination imaging data properly orientated, the method 188 includes converting the single class segmentation mask to a multi-class segmentation mask (e.g., 4 class mask) based on the laterality so that different regions of the region of interest are labeled with different segmentation masks for both the source medical imaging data and the destination medical imaging data (block 226). In certain embodiments, a heuristic approach is utilized to convert the single class segmentation mask to multi-class segmentation mask. In certain embodiments, a trained deep learning-based segmentation model is utilized to convert the single class segmentation mask to multi-class segmentation mask. In certain embodiments, the different regions include different meniscus horns (e.g., lateral anterior horn, lateral posterior horn, medial anterior horn, and medial posterior horn). In certain embodiments, each horn is labeled as a separate class with a different segmentation mask. FIG. 6 depicts MR images 228 and 230 illustrating meniscus segmentation masks converted from a single class to four classes. In particular, FIG. 6 depicts the conversion of a single label for all meniscus horns into 4 different labels namely medial anterior horn, medial posterior horn, lateral anterior horn and lateral posterior horn. The MR images 228 and 230 of a knee were acquired with a MR scanner utilizing a 3D fast spin echo sequence. MR image 230 is the same as MR image 228. In the MR image 228, all of the meniscus horns are labeled as a single segmentation mask. In the MR image 230, each of the different meniscus horns (e.g., lateral anterior horn, lateral posterior horn, medial anterior horn, and medial posterior horn) are labeled with different segmentation masks. The MR images 228 and 230 are sagittal views of the knee. Image 232 is a 3D rendering of all four of the segmented meniscus horns alone with the single segmentation mask. Image 234 is a 3D rendering of all four of the segmented meniscus horns different segmentation masks.

Returning to FIG. 3, the method 188 includes selecting a region from the different regions from the source medical imaging data for transplantation (which in turn results in the selection of a corresponding region in the source destination medical imaging to replace with the selected region) (block 236). In certain embodiments, the selected region is one of the meniscus horns (e.g., lateral anterior horn, lateral posterior horn, medial anterior horn, or medial posterior horn) having a particular feature (e.g., lesion). The corresponding region (e.g., corresponding meniscus horn) is healthy (i.e., lacks a lesion). In certain embodiments, the selected region may be chosen due to having an interesting lesion that is desired to replicate in order to increase its representativeness. In certain embodiments, the region may be selected randomly. In certain embodiments, the region may be selected based on a particular region having a particular feature that deep learning-based segmentation models have trouble segmenting.

The method 188 also includes spatially matching the region in the source medical imaging data to the corresponding region in the destination medical imaging data (block 238). In certain embodiments, as described in greater detail below, spatially matching the region in the source medical imaging data to the corresponding region in the destination medical imaging data includes computing a first centroid from a source segmentation mask of the region; computing a second centroid from a destination segmentation mask of the corresponding region; computing a Cartesian difference between the first centroid and the second centroid in all three dimensions; spatially fixing the destination medical imaging data and the destination segmentation mask; and translating the source medical imaging data and the source segmentation mask to spatially match with the destination medical imaging data and the destination segmentation mask utilizing the Cartesian difference between the first centroid and the second centroid in all three dimensions.

Upon spatial matching of the centroids in the source medical imaging data and the destination medical imaging data, the method 188 further includes determining a spatial intersection between the region in the source medical imaging data and the corresponding region in the destination medical imaging data utilizing respective segmentation masks for the region and the corresponding region (block 240). Only the spatial intersection between source and destination segmentations is utilized to crop the medical imaging data.

Figure 7:
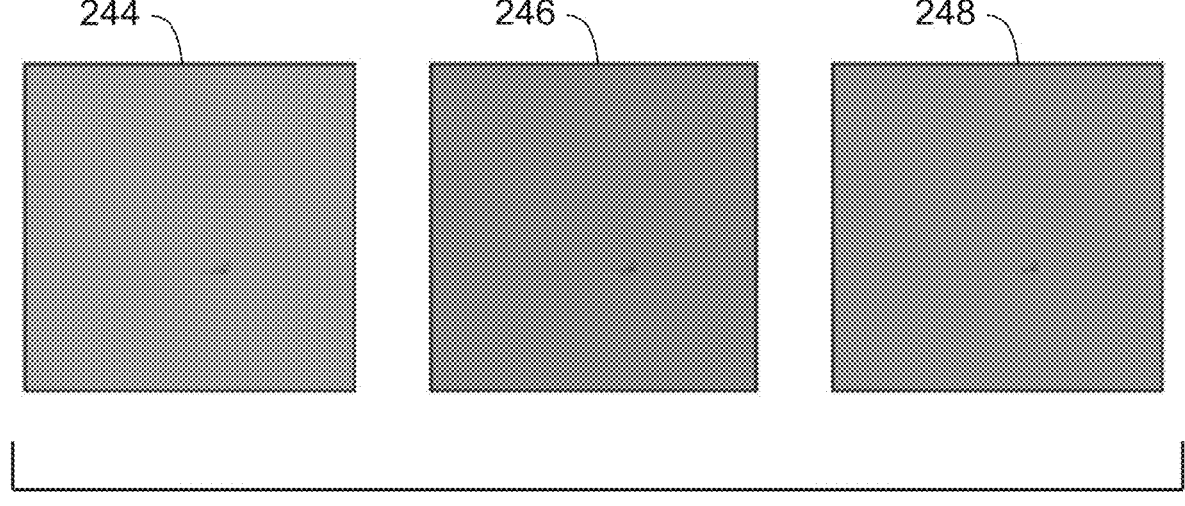
FIG. 7 depicts MR images of different slices of a source medical imaging volume (e.g., source MRI volume) illustrating where the whole of each MR image is zeroed out except for the region inside an intersection mask, in accordance with aspects of the present disclosure.

The method 188 even further includes utilizing an intersection mask of the spatial intersection to crop a first portion of the region overlapping with the intersection mask (e.g., selected source meniscus horn) from the source medical imaging data for transplantation in the destination medical imaging data (block 242). In certain embodiments, utilizing the intersection mask of the spatial intersection to crop (e.g., cut) the first portion of the region overlapping with the intersection mask from the source medical imaging data includes multiplying the source medical imaging data by an intersecting data corresponding to the intersection mask to generate a first imaging data where only pixel intensities of pixels (e.g., 2D pixel or 3D pixel (i.e., a voxel)) of the source medical imaging data within the intersection mask are kept. The final data should be all zeros for the pixel intensities except for the pixels inside the 3D region delimited by the intersection mask (which should contain the pixels of the original source image). FIG. 7 illustrates MR images 244, 246, and 248 of different slices of the source medical imaging data (e.g., source MRI data) where the whole of each MR image 244, 246, and 248 is zeroed out except for the region inside the intersection mask.

The method 188 includes utilizing the intersection mask of the spatial intersection to remove a second portion of the destination medical imaging data in the corresponding region that overlaps with the intersection mask (i.e., cut a hole in the destination medical imaging data for transplanting or inserting the source meniscus horn) (block 250). In certain embodiments, utilizing the intersection mask of the spatial intersection to remove a second portion of the destination medical imaging data in the corresponding region that overlaps with the intersection mask includes multiplying the destination medical imaging data by an inverse of the intersecting data to generate a second imaging data where pixel intensities of pixels of the destination medical imaging data outside the intersection mask are kept and pixels within the intersection mask are zeroed out. The final data should be equal to the destination except for the pixels inside the 3D region delimited by the intersection mask. This region must contain all zeros so that it can be filled by the pixels extracted in block 242.

The method 188 also includes adding (e.g., combining) the first portion of the region from the source medical imaging data into the destination medical imaging data where the second portion was removed to generate an augmented version of the destination medical imaging data (block 252). In the final augmented imaging data, the meniscus horn is going to belong to the source imaging data and all surrounding pixel intensities are going to be from the destination medical imaging data. The method 188 further includes saving/storing the final augmented imaging data (which is an alternate augmented version of the original destination medical imaging data) (block 254). The final augmented imaging data can be paired with the original segmentation label for the meniscus where there are manual labels for the original destination medical imaging data. The blocks 236, 238, 240, 242, 250, 252, and 254 may be repeated one or more times for one or more other regions (e.g., meniscus horns) to generate more augmented imaging data.

The final augmented imaging data may be utilized to update the training of the trained deep learning-based segmentation model utilized in block 192. The method 188 includes utilize the augmented version of the destination medical imaging data to update training of trained deep learning-based segmentation model to be configured to segment meniscus horns having lesions (block 256).

Figure 8:
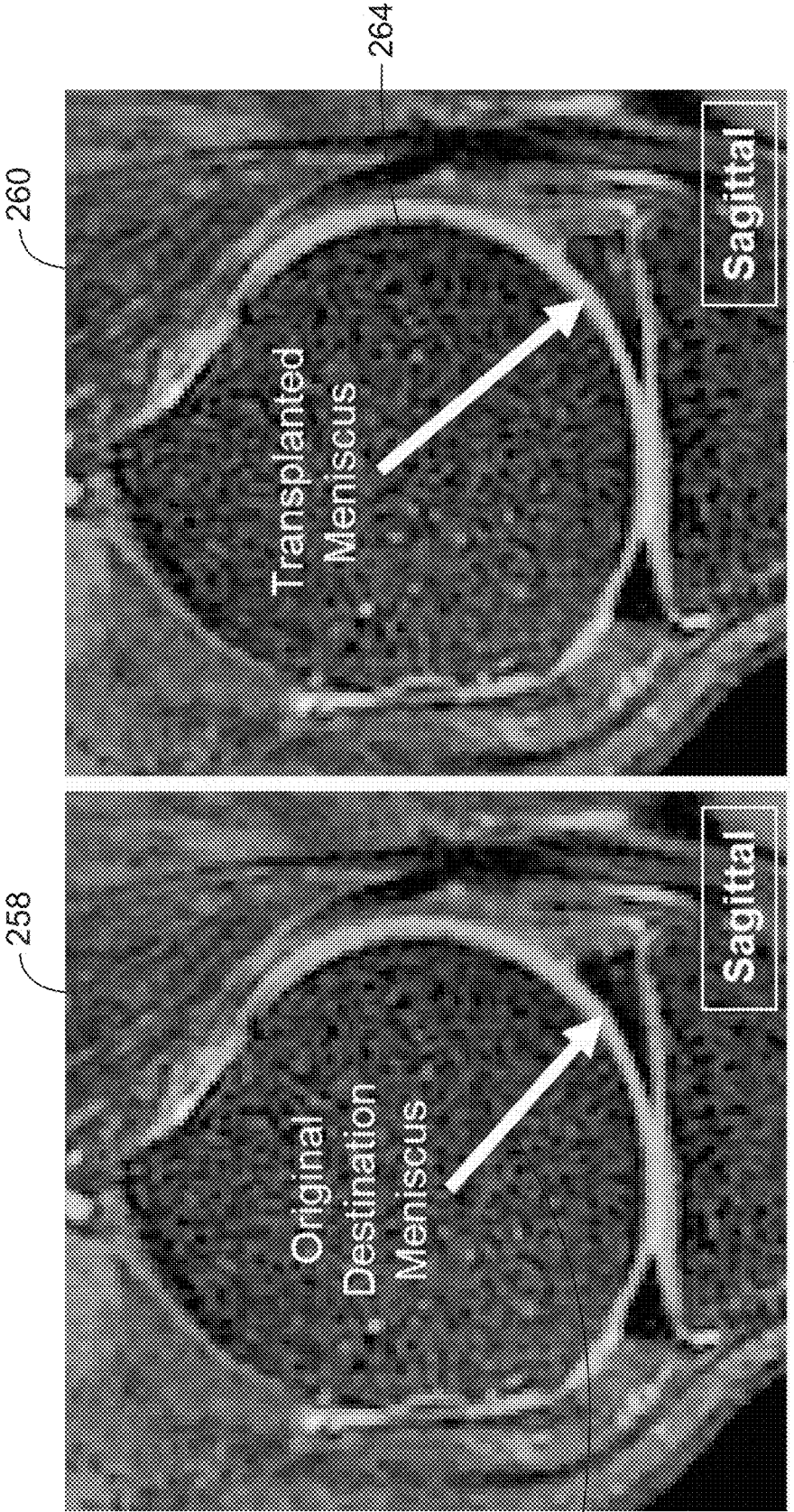
FIG. 8 depicts sagittal views of a destination MR image of a knee and an augmented version of the destination MR image, in accordance with aspects of the present disclosure.

FIG. 8 depicts sagittal views of a destination MR image 258 of a knee and an augmented version 260 of the destination MR image 258. Arrow 262 indicates the original destination meniscus horn in destination MR image 258. The augmented version 260 has a transplanted meniscus horn as indicate by arrow 264.

FIG. 9 depicts coronal views of a destination MR image 266 of the same knee and an augmented version 268 of the destination MR image 266. Arrow 270 indicates the original destination meniscus horn in destination MR image 266. The augmented version 268 has a transplanted meniscus horn as indicated by arrow 272.

Figure 10:
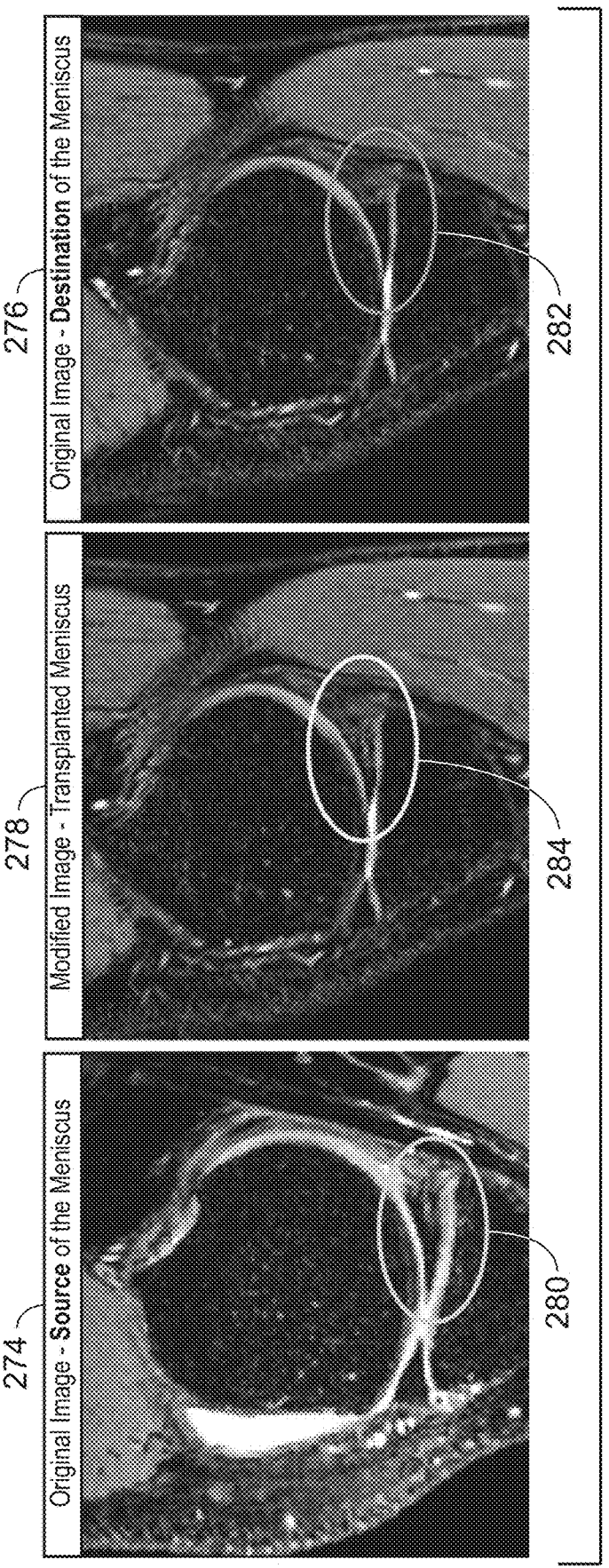
FIG. 10 depicts sagittal views of a source MR image of a knee, a destination MR image of another knee, and an augmented version of the destination MR image, in accordance with aspects of the present disclosure.

FIG. 10 depicts sagittal views of a source MR image 274 of a knee, a destination MR image 276 of another knee, and an augmented version 278 of the destination MR image. Ellipsis 280 in the source MR image 274 indicates a source meniscus horn (which has a lesion) to be transplanted into the destination MR image 276. Ellipsis 282 in the destination MR image 276 indicates the meniscus horn (which is healthy and lacks a lesion) that is to be replaced by the source meniscus horn. Ellipsis 284 in the augmented version 278 indicates the transplanted source meniscus horn.

FIG. 11 illustrates a flow diagram of a method 286 for spatially matching a region in a source medical imaging data to a corresponding region in a destination medical imaging data. One or more steps of the method 286 may be performed by processing circuitry of the magnetic resonance imaging system 100 in FIG. 1 or a remote computing device. One or more of the steps of the method 286 may be performed simultaneously or in a different order from the order depicted in FIG. 11. One or more (and in some cases) all of the steps of the method 286 may be performed automatically.

The method 286 includes computing a first centroid from a source segmentation mask of the region (block 288). The method 286 also includes computing a second centroid from a destination segmentation mask of the corresponding region (block 290). The method 286 further includes computing a Cartesian difference between the first centroid and the second centroid in all three dimensions (block 292). The method 286 even further includes spatially fixing the destination medical imaging data and the destination segmentation mask (block 294). The method 286 yet further includes translating the source medical imaging data and the source segmentation mask to spatially match with the destination medical imaging data and the destination segmentation mask utilizing the Cartesian difference between the first centroid and the second centroid in all three dimensions (block 296).

Figure 12:
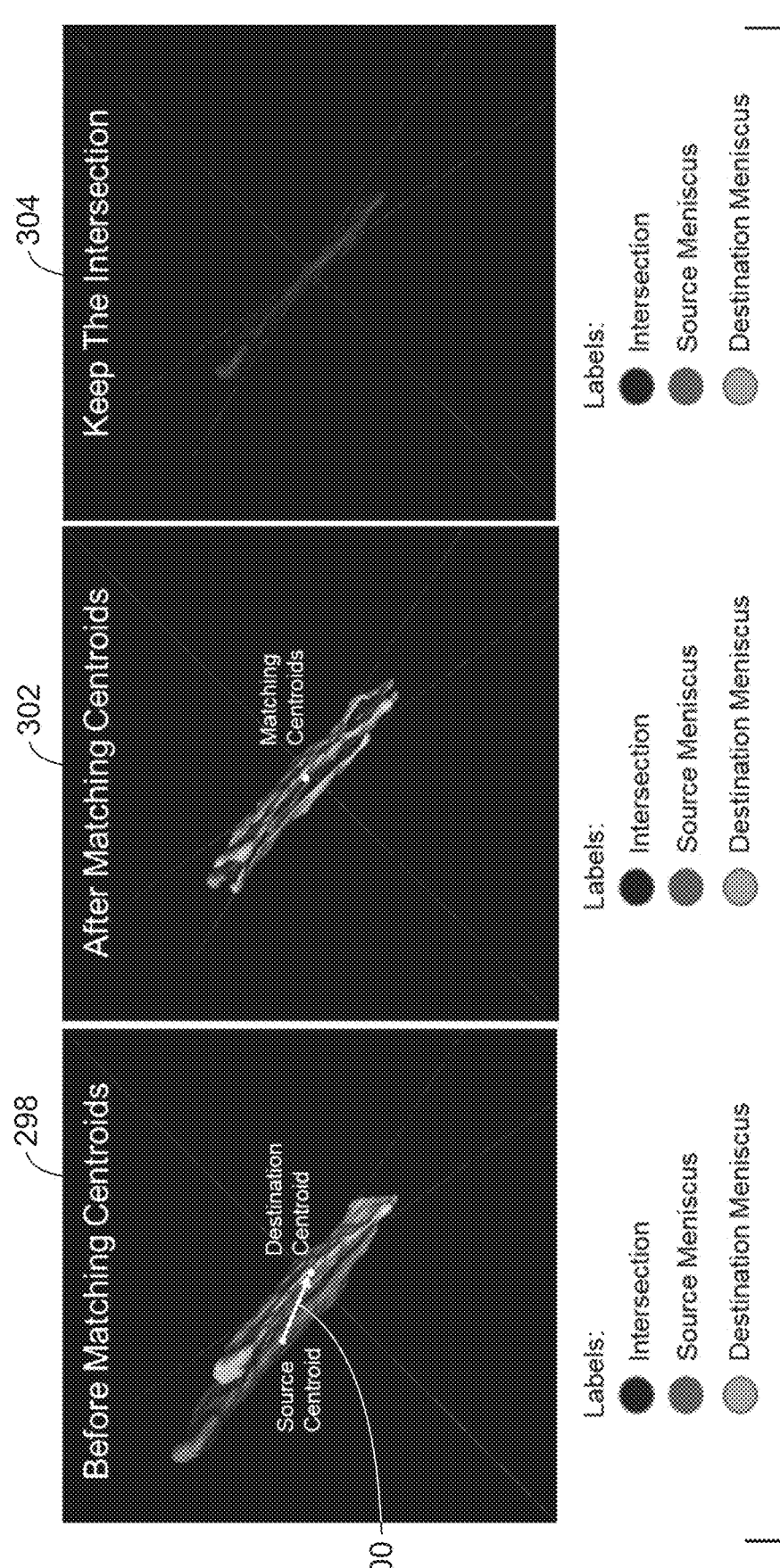
FIG. 12 depicts images of 3D renderings of source and destination segmentation masks and its corresponding centroids before matching, centroids after matching, and the kept intersection segmented region after matching centroids, in accordance with aspects of the present disclosure.

FIG. 12 depicts images of 3D renderings of source and destination segmentation masks and its corresponding centroids before matching, centroids after matching, and the kept segmented region intersection after matching centroids. Image 298 is a 3D rendering before the matching of centroids (source centroid (e.g., first centroid) and destination centroid (e.g., second centroid). Arrow 300 in image 298 indicates how source centroid of source meniscus segmentation will be translated relative to the destination centroid of the destination meniscus segmentation. Image 302 is a 3D rendering after the matching of the centroids. Image 304 is a 3D rendering of the spatial intersection of the centroids that is kept that forms the intersection mask.

Figure 13:
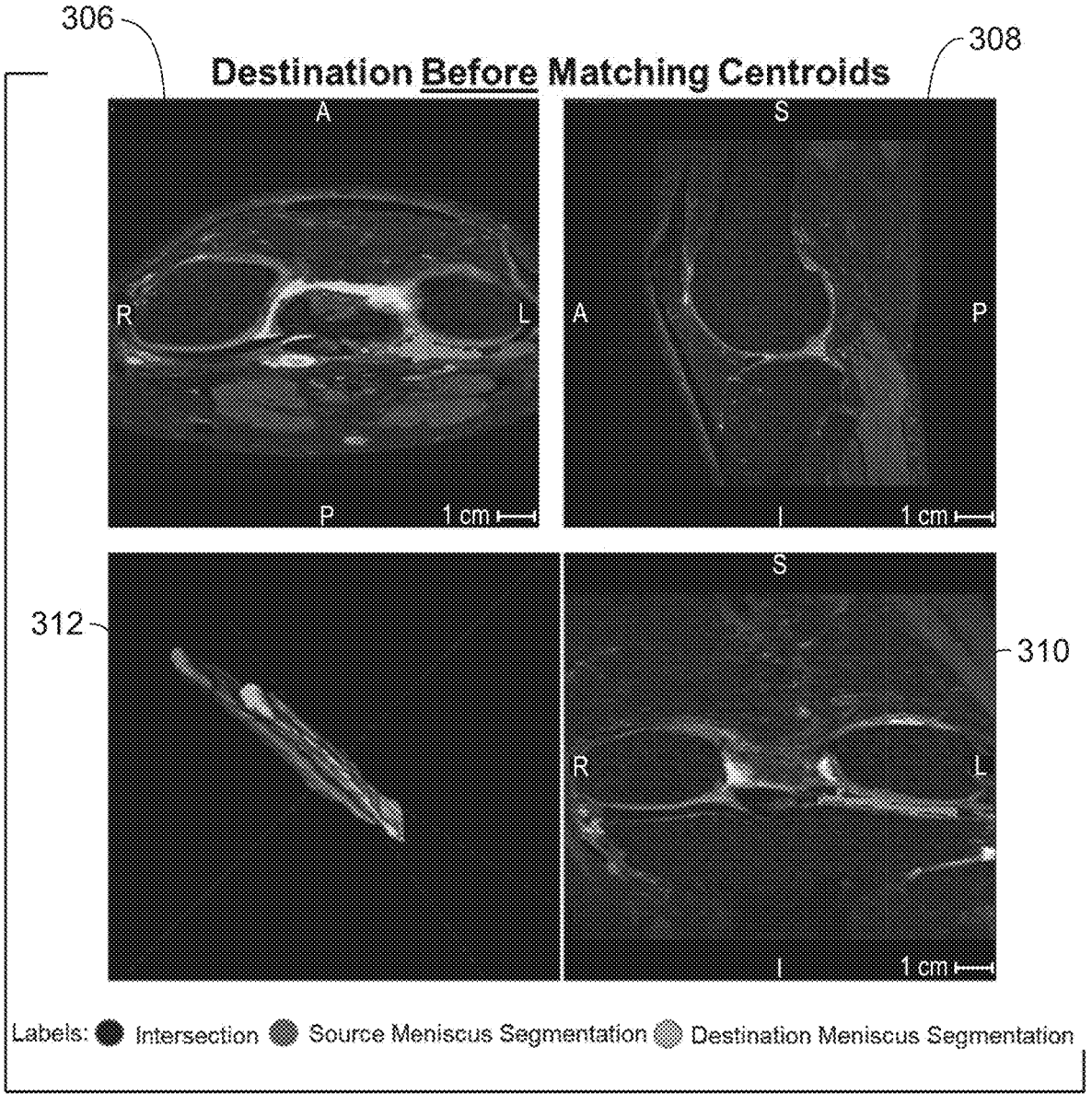
FIG. 13 depicts different views of a destination MR image of knee before matching of centroids, in accordance with aspects of the present disclosure.

FIG. 13 depicts different views of a destination MR image of knee before matching of centroids. The MR images 306, 308, and 310 are axial, sagittal, and coronal views, respectively, of the knee. The source meniscus segmentation, the destination meniscus segmentation, and the spatial intersection between these segmentations are indicated in the MR images 306, 308, and 310. Image 312 is a 3D rendering of just the segmentations and the spatial intersection.

Figure 14:
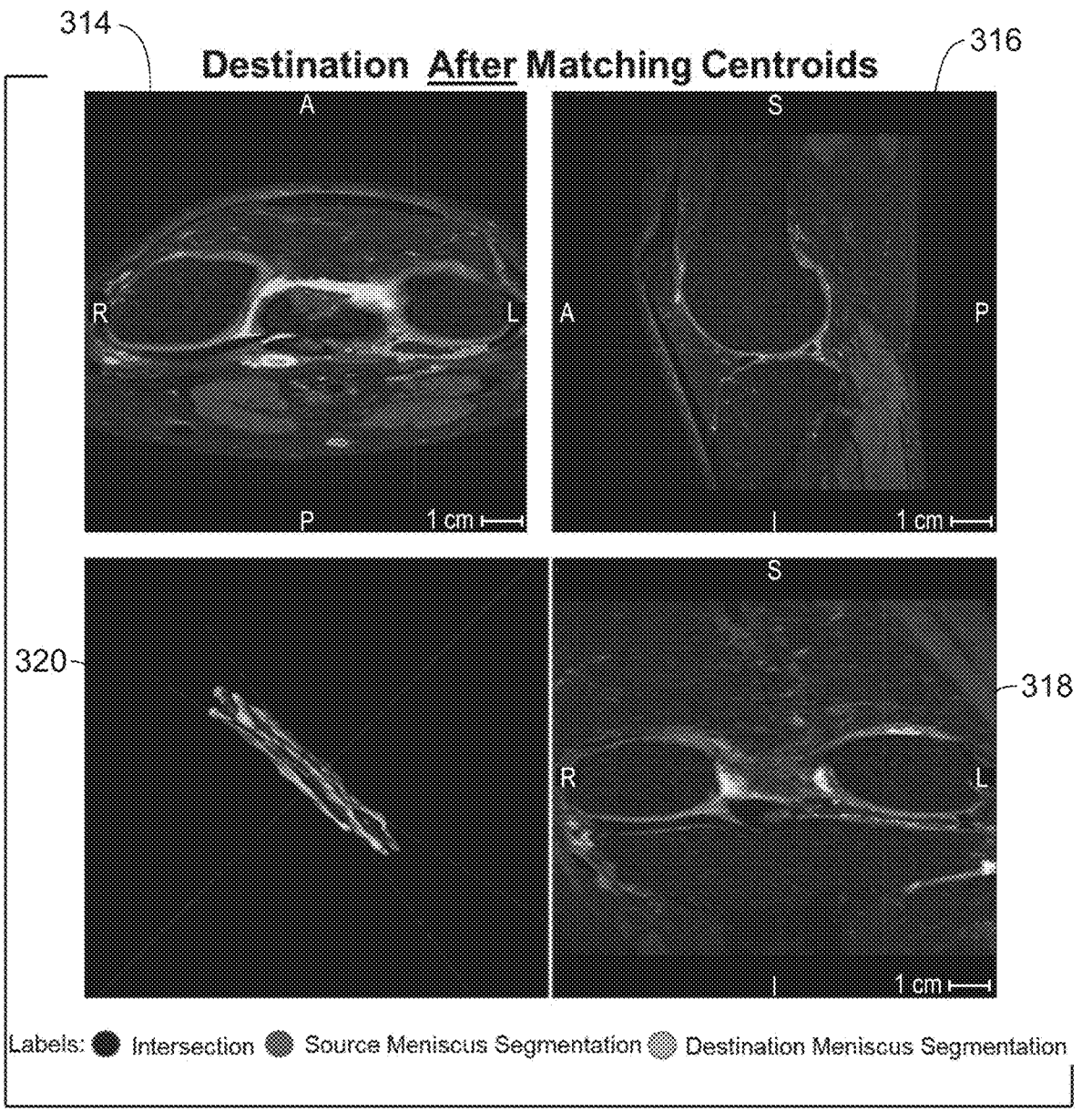
FIG. 14 depicts different views of a destination MR image of knee after matching of centroids, in accordance with aspects of the present disclosure.

FIG. 14 depicts different views of a destination MR image of knee after matching of centroids. The MR images 314, 316, and 318 are axial, sagittal, and coronal views, respectively, of the same knee in FIG. 13. The source meniscus segmentation, the destination meniscus segmentation, and the spatial intersection between these segmentations are indicated in the MR images 314, 316, and 318. Image 320 is a 3D rendering of just the segmentations and the spatial intersection.

Figure 15:
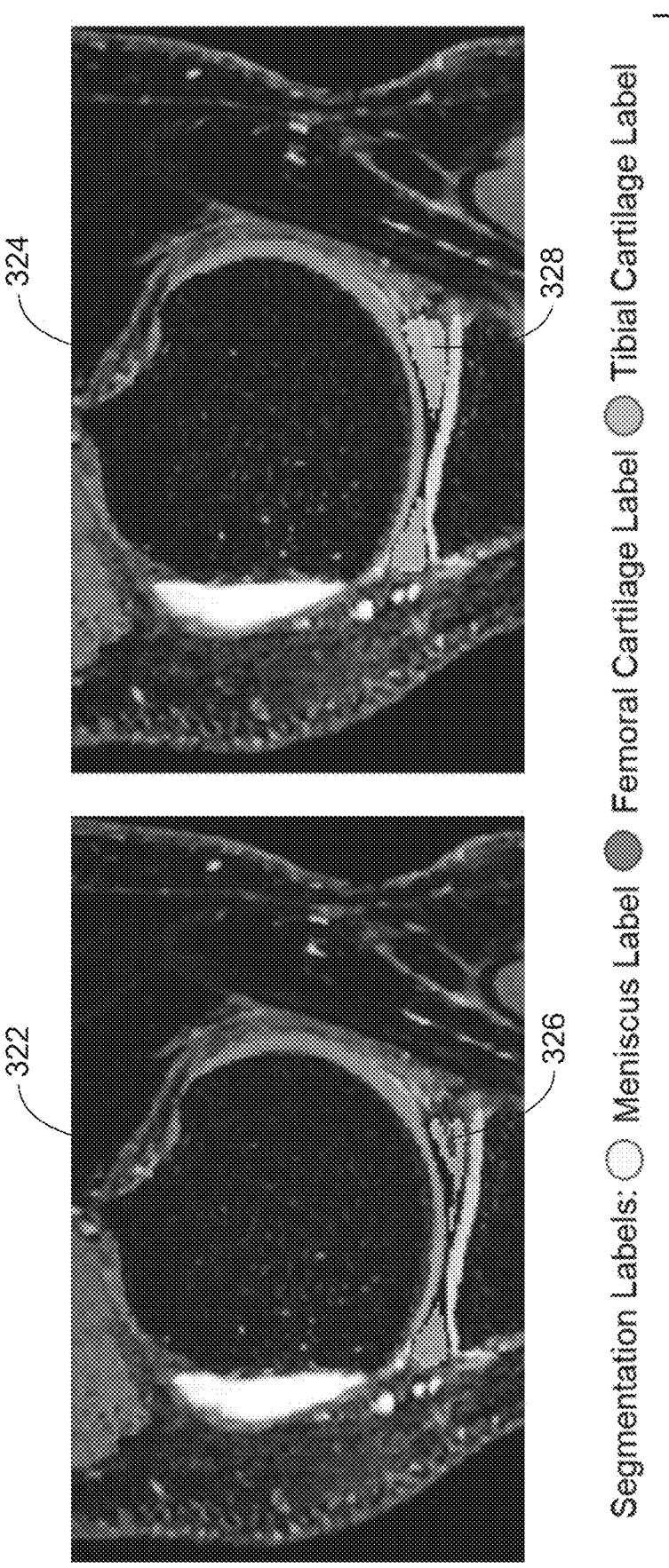
FIG. 15 depicts MR images of a knee comparing the performance between a baseline segmentation deep learning-based segmentation model and an updated deep learning-based segmentation model, in accordance with aspects of the present disclosure.

As noted above, the augmented medical imaging volumes can be utilized to update the training of deep learning-based segmentation models. FIG. 15 depicts MR images 322, 324 of a knee with segmentation masks comparing the performance between a baseline segmentation deep learning-based segmentation model and an updated deep learning-based segmentation model. The baseline segmentation model is a 5 class (e.g., background, patellar cartilage, femoral cartilage, tibial cartilage, and meniscus) segmentation model. The baseline segmentation model includes a V-Net architecture and was trained from scratch on with MR imaging data of knees acquired with double echo steady state (DESS) sequences that have manual segmentations and validated with similar MR imaging data. MR imaging data acquired with 3D fast spin echo sequences and previously labeled with weak segmentation labels by a previous segmentation model were used to finetune the baseline segmentation model. Manually segmented MR imaging data were utilized for validation. Finally, manually segmented MR imaging volumes acquired with 3D fast spin echo sequences were utilized to finetune the baseline segmentation model.

The updated segmentation model is similar to the baseline segmentation model described above but the updated segmentation model had the last finetuning step modified from above. In particular of 20 training cases utilized for finetuning the baseline segmentation model, 6 cases with more meniscus injuries were utilized as source imaging volumes. The meniscus transplantation technique described above was applied 60 percent of the time during training of the updated segmentation model Thus, for each new image in the batch, a random source from the source imaging volumes was chosen and a random number of transplants (e.g., from 1 to 4) were chosen from the randomly selected source for transplant into the destination. The augmented imaging volumes (e.g., with meniscus horns with lesions) were utilized in the training (e.g., finetuning) of the updated segmentation model.

MR images 322, 324 were derived from the same slice of 3D MR imaging volume of a knee. MR image 322 was output from the baseline segmentation deep learning-based segmentation model. MR image 324 was output from the updated deep learning-based segmentation model. In MR image 322, the baseline deep learning-based segmentation model segmented around the lesion on the medial posterior meniscus horn (as indicated by arrow 326), as the meniscus is normally a dark region in the image. In particular, as shown in the MR image 322, the brighter signal of the lesion was dimmed by the baseline deep learning-based segmentation model to be background and, thus, was not segmented. In contrast, as indicated by arrow 328, in the MR image 324, the updated deep learning-based segmentation model segmented the entire meniscus including the medial posterior meniscus horn having the lesion.

Technical effects of the disclosed subject matter include providing for a topological-based methodology for augmenting (e.g., both automatically and artificially) a training set and increasing data variety (which in turn increase segmentation model accuracy). In particular, the technical effects of the disclosed subject matter include enabling augmentation of MRI 3D datasets of the knee (e.g., acquired with a 3D fast spin echo sequence) or MRI 2D datasets of the knee with many instances of different type of menisci by copying this region of interest from one case and seamlessly pasting it in another case. Technical effects of the disclosed subject matter further include enabling the copying of lesions from cases where there are known menisci lesions and include lesions in other where the menisci are healthy. Technical effects of the disclosed subject matter include providing an augmentation technique that increases data variety by increasing the representativeness of lesion patterns that are less common for anomaly detection (i.e., lesion detection). Technical effects of the disclosed subject matter also include utilizing real image features from multiple and combining them into one modified/augmented new image, thus, avoiding the drawbacks of generative-adversarial techniques that generate artificial medical images (i.e., creating image features that are not representative real life). Technical effects of the disclosed subject matter include reducing cost and saving time by avoiding having to collect extra data or manually labeling more data, while also increasing the performance of existing deep learning-based segmentation models (via increasing the variety of data for training). Technical effects of the disclosed subject matter include increasing both quantitatively and qualitatively the accuracy of the deep learning-based segmentation compared to the original deep-learning based segmentation approaches. Technical effects of the disclosed subject matter include providing more accurate thickness measurements and better localized anomaly detection due to more accurate segmentations, thus, benefiting the patient.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for generating a variety of data for training a deep learning-based segmentation model, comprising:

obtaining, at a processor, both a source medical imaging data and a destination medical imaging data having an anatomical region;

segmenting, via the processor, a region of interest in the anatomical region in both the source medical imaging data and the destination medical imaging data utilizing a trained deep learning-based segmentation model, wherein the region of interest is labeled with a single segmentation mask;

determining, via the processor, a laterality of the anatomical region in both the source medical imaging data and the destination medical imaging data;

converting, via the processor, the single segmentation mask to a multi-class segmentation mask based on the laterality so that different regions of the region of interest are labeled with different segmentation masks for both the source medical imaging data and the destination medical imaging data;

selecting, via the processor, a region from the different regions from the source medical imaging data for transplantation;

spatially matching, via the processor, the region in the source medical imaging data to a corresponding region in the destination medical imaging data;

determining, via the processor, a spatial intersection between the region in the source medical imaging data and the corresponding region in the destination medical imaging data utilizing respective segmentation masks for the region and the corresponding region;

utilizing, via the processor, an intersection mask of the spatial intersection to crop a first portion of the region overlapping with the intersection mask from the source medical imaging data for transplantation in the destination medical imaging data;

utilizing, via the processor, the intersection mask of the spatial intersection to remove a second portion of the destination medical imaging data in the corresponding region that overlaps with the intersection mask; and adding, via the processor, the first portion of the region from the source medical imaging data into the destination medical imaging data where the second portion was removed to generate an augmented version of the destination medical imaging data.

2. The computer-implemented method of claim 1, wherein the source medical imaging data and the destination medical imaging data comprise magnetic resonance imaging data.

3. The computer-implemented method of claim 2, wherein the region of interest comprises a meniscus, the anatomical region comprises a knee, and the different regions comprise different meniscus horns.

4. The computer-implemented method of claim 3, wherein the region selected from the different regions comprises a meniscus horn having a lesion and the corresponding region comprises a corresponding meniscus horn to the meniscus horn having the lesion, and the corresponding meniscus horn lacks a lesion.

5. The computer-implemented method of claim 4, further comprising utilizing, via the processor, the augmented version of the destination medical imaging data to update training of the trained deep learning-based segmentation model to be configured to segment meniscus horns having lesions.

6. The computer-implemented method of claim 1, wherein spatially matching the region in the source medical imaging data to the corresponding region in the destination medical imaging data comprises:

computing, via the processor, a first centroid from a source segmentation mask of the region;

computing, via the processor, a second centroid from a destination segmentation mask of the corresponding region;

computing, via the processor, a Cartesian difference between the first centroid and the second centroid in all three dimensions;

spatially fixing, via the processor, the destination medical imaging data and the destination segmentation mask; and translating, via the processor, the source medical imaging data and the source segmentation mask to spatially match with the destination medical imaging data and the destination segmentation mask utilizing the Cartesian difference between the first centroid and the second centroid in all three dimensions.

7. The computer-implemented method of claim 1, wherein utilizing the intersection mask of the spatial intersection to crop the first portion of the region overlapping with the intersection mask from the source medical imaging data comprises multiplying the source medical imaging data by an intersecting data corresponding to the intersection mask to generate a first imaging data where only pixel intensities of pixels of the source medical imaging data within the intersection mask are kept.

8. The computer-implemented method of claim 7, wherein utilizing the intersection mask of the spatial intersection to remove a second portion of the destination medical imaging data in the corresponding region that overlaps with the intersection mask comprises multiplying the destination medical imaging data by an inverse of the intersecting data to generate a second imaging data where pixel intensities of pixels of the destination medical imaging data outside the intersection mask are kept and pixels within the intersection mask are zeroed out.

9. A system for generating a variety of data for training a deep learning-based segmentation model, comprising:
  a memory encoding processor-executable routines; and
  a processor configured to access the memory and to execute the processor-executable routines, wherein the processor-executable routines, when executed by the processor, cause the processor to:
    obtain both a source medical imaging data and a destination medical imaging data having an anatomical region;
    segment a region of interest in the anatomical region in both the source medical imaging data and the destination medical imaging data utilizing a trained deep learning-based segmentation model, wherein the region of interest is labeled with a single segmentation mask;
    determine a laterality of the anatomical region in both the source medical imaging data and the destination medical imaging data;
    convert the single segmentation mask to a multi-class segmentation mask based on the laterality so that different regions of the region of interest are labeled with different segmentation masks for both the source medical imaging data and the destination medical imaging data;
    select a region from the different regions from the source medical imaging data for transplantation;
    spatially match the region in the source medical imaging data to a corresponding region in the destination medical imaging data;
    determine a spatial intersection between the region in the source medical imaging data and the corresponding region in the destination medical imaging data utilizing respective segmentation masks for the region and the corresponding region;
    utilize an intersection mask of the spatial intersection to crop a first portion of the region overlapping with the intersection mask from the source medical imaging data for transplantation in the destination medical imaging data;
    utilize the intersection mask of the spatial intersection to remove a second portion of the destination medical imaging data in the corresponding region that overlaps with the intersection mask; and
    add the first portion of the region from the source medical imaging data into the destination medical imaging data where the second portion was removed to generate an augmented version of the destination medical imaging data.

10. The system of claim 9, wherein the source medical imaging data and the destination medical imaging data comprise magnetic resonance imaging data.

11. The system of claim 10, wherein the region of interest comprises a meniscus, the anatomical region comprises a knee, and the different regions comprise different meniscus horns.

12. The system of claim 11, wherein the region selected from the different regions comprises a meniscus horn having a lesion and the corresponding region comprises a corresponding meniscus horn to the meniscus horn having the lesion, and the corresponding meniscus horn lacks a lesion.

13. The system of claim 12, wherein the processor-executable routines, when executed by the processor, further cause the processor to utilize the augmented version of the destination medical imaging data to update training of the trained deep learning-based segmentation model to be configured to segment meniscus horns having lesions.

14. The system of claim 9, wherein spatially matching the region in the source medical imaging data to the corresponding region in the destination medical imaging data comprises:
    computing a first centroid from a source segmentation mask of the region;
    computing a second centroid from a destination segmentation mask of the corresponding region;
    computing a Cartesian difference between the first centroid and the second centroid in all three dimensions;
    spatially fixing the destination medical imaging data and the destination segmentation mask; and
    translating the source medical imaging data and the source segmentation mask to spatially match with the destination medical imaging data and the destination segmentation mask utilizing the Cartesian difference between the first centroid and the second centroid in all three dimensions.

15. The system of claim 9, wherein utilizing the intersection mask of the spatial intersection to crop the first portion of the region overlapping with the intersection mask from the source medical imaging data comprises multiplying the source medical imaging data by an intersecting data corresponding to the intersection mask to generate a first imaging data where only pixel intensities of pixels of the source medical imaging data within the intersection mask are kept.

16. The system claim 15, wherein utilizing the intersection mask of the spatial intersection to remove a second portion of the destination medical imaging data in the corresponding region that overlaps with the intersection mask comprises multiplying the destination medical imaging data by an inverse of the intersecting data to generate a second imaging data where pixel intensities of pixels of the destination medical imaging data outside the intersection mask are kept and pixels within the intersection mask are zeroed out.

17. A non-transitory computer-readable medium, the non-transitory computer-readable medium comprising processor-executable code that when executed by a processor, causes the processor to:
    obtain both a source medical imaging data and a destination medical imaging data having an anatomical region;
    segment a region of interest in the anatomical region in both the source medical imaging data and the destination medical imaging data utilizing a trained deep learning-based segmentation model, wherein the region of interest is labeled with a single segmentation mask;
    determine a laterality of the anatomical region in both the source medical imaging data and the destination medical imaging data;

convert the single segmentation mask to a multi-class segmentation mask based on the laterality so that different regions of the region of interest are labeled with different segmentation masks for both the source medical imaging data and the destination medical imaging data;

select a region from the different regions from the source medical imaging data for transplantation;

spatially match the region in the source medical imaging data to a corresponding region in the destination medical imaging data;

determine a spatial intersection between the region in the source medical imaging data and the corresponding region in the destination medical imaging data utilizing respective segmentation masks for the region and the corresponding region;

utilize an intersection mask of the spatial intersection to crop a first portion of the region overlapping with the intersection mask from the source medical imaging data for transplantation in the destination medical imaging data;

utilize the intersection mask of the spatial intersection to remove a second portion of the destination medical imaging data in the corresponding region that overlaps with the intersection mask; and add the first portion of the region from the source medical imaging data into the destination medical imaging data where the second portion was removed to generate an augmented version of the destination medical imaging data.

18. The non-transitory computer-readable medium of claim 17, wherein the source medical imaging data and the destination medical imaging data comprise magnetic resonance imaging data, and wherein the region of interest comprises a meniscus, the anatomical region comprises a knee, and the different regions comprise different meniscus horns.

19. The non-transitory computer-readable medium of claim 18, wherein the region selected from the different regions comprises a meniscus horn having a lesion and the corresponding region comprises a corresponding meniscus horn to the meniscus horn having the lesion, and the corresponding meniscus horn lacks a lesion.

20. The non-transitory computer-readable medium of claim 19, wherein the processor-executable code, when executed by the processor, further cause the processor to utilize the augmented version of the destination medical imaging data to update training of the trained deep learning-based segmentation model to be configured to segment meniscus horns having lesions.

* * * * *